Figure 1:
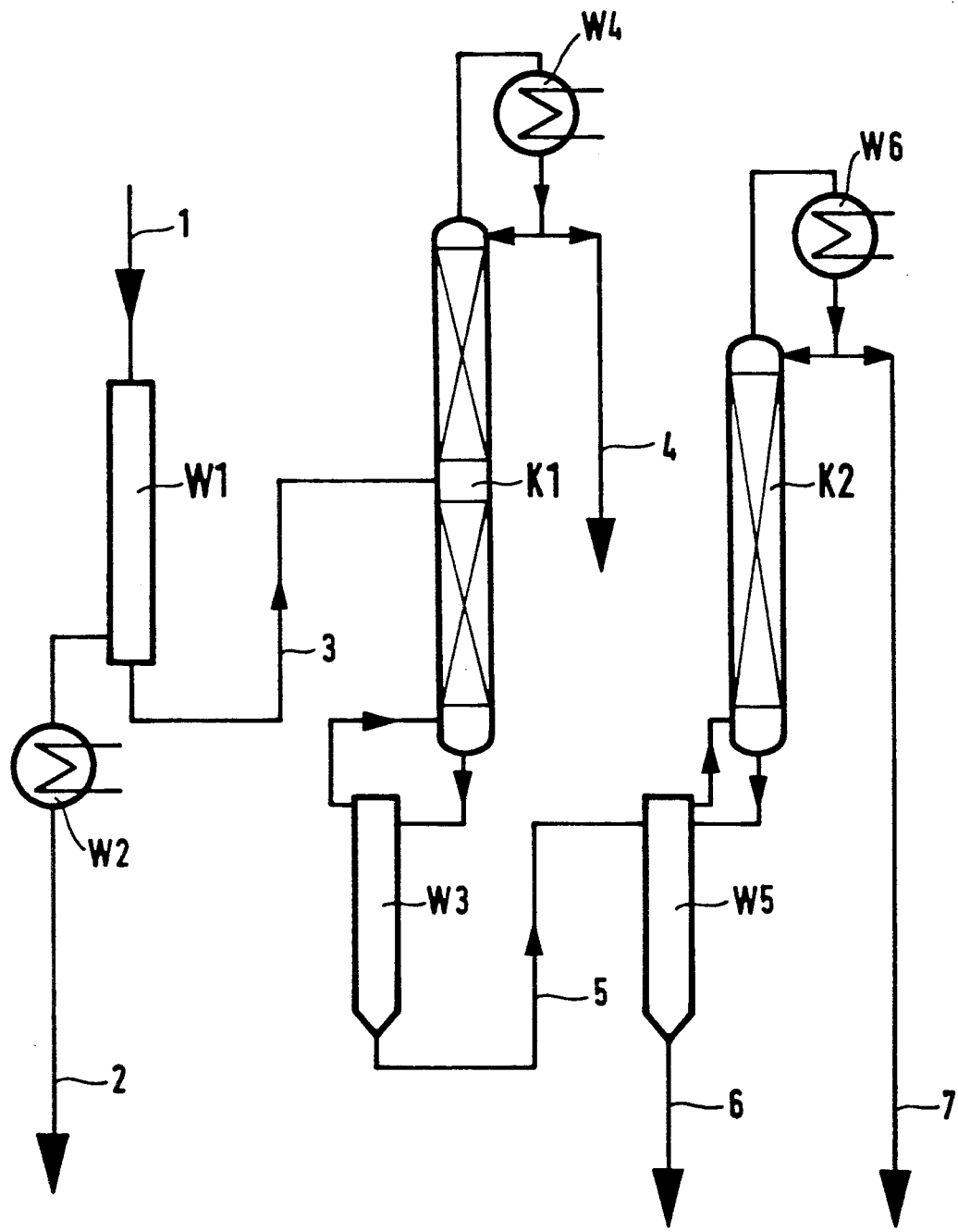

United States Patent [19]

Kovàsy et al.

[11] Patent Number: 5,130,465
[45] Date of Patent: Jul. 14, 1992

[54] PROCESS FOR THE PREPARATION OF HYDROXYPHENYLPROPIONATES

[75] Inventors: Kàlmàn Kovàsy, Bottmingen; Zdenek Mazour, Lausen, both of Switzerland

[73] Assignee: Ciba-Geigy Corporation, Ardsley, N.Y.

[21] Appl. No.: 675,359

[22] Filed: Mar. 22, 1991

[30] Foreign Application Priority Data

Mar. 30, 1990 [CH] Switzerland .................. 1058/90

[51] Int. Cl.$^5$ .................................................. C07C 69/76
[52] U.S. Cl. ........................................................ 560/75
[58] Field of Search ........................................ 560/75

[56] References Cited

U.S. PATENT DOCUMENTS 3,330,859 4/1967 Dexter et al. .................. 560/225
3,364,250 1/1968 Dexter et al. .................. 560/75

FOREIGN PATENT DOCUMENTS

WO86/00301 1/1986 PCT Int'l Appl. .

OTHER PUBLICATIONS

Chem. Abst. 104, 10923w.

Primary Examiner—Paul J. Killos
Attorney, Agent, or Firm—Luther A. R. Hall

[57] ABSTRACT

Hydroxyphenylpropionates are prepared by Michael addition of an acrylic acid component to a phenol component. The compounds are purified by vacuum rectification after separation of the basic catalyst.

11 Claims, 2 Drawing Sheets

PROCESS FOR THE PREPARATION OF HYDROXYPHENYLPROPIONATES

The present invention relates to a novel process for the preparation of hydroxyphenylpropionates.

Hydroxyphenylpropionates are normally prepared by the "Michael addition" of a phenol and an alkylacrylate in the presence of a basic catalyst, as disclosed, for example, in DE-A-3 390 557. The adducts, i.e. hydroxyphenylpropionates, can then be freed from by-products by crystallisation or, as described in U.S. Pat. No. 3,330,859 and U.S. Pat. No. 3,364,250, also by distillation.

The hydroxyphenylpropionates so obtained are important intermediates for the preparation of antioxidants for synthetic polymers, especially for the polyolefins described in the above publications. By altering the molecular weight of the ester group it is possible to meet specific requirements which are made of an antioxidant, for example low volatility. This alteration can be effected direct by the synthesis or also indirectly, for example by transesterifying an already prepared hydroxyphenylpropionate.

It has now been found that the process can be substantially improved, especially with respect to yield and purity of the final product, by a combination of specific measures, namely neutralising the basic catalyst by a carboxylic acid, removing the salt so formed from the reaction mixture, and subsequently rectifying the filtrate.

Accordingly, the invention relates to a process for the preparation of compounds of formula

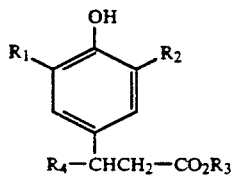

(1)

by reacting compounds of formula

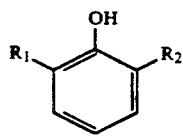

(2)

with compounds of formula

(3)

wherein the substituents $R_1$ to $R_3$ in formulae (1) to (3) are each independently of the other alkyl of 1 to 4 carbon atoms, and $R_4$ is hydrogen or alkyl of 1 to 4 carbon atoms, in the presence of a base, and isolating the compounds of formula (1), which process comprises adding a carboxylic acid to the reaction mixture to neutralise the base after the reaction of a compound of formula (2) with a compound of formula (3) and before the isolation of a compound of formula (1), filtering the reaction mixture, and rectifying the filtrate to isolate the compound of formula (1).

In the compounds of formula (1), the substituents $R_1$ to $R_3$ are each independently of the other alkyl of 1 to 4 carbon atoms, typically methyl, ethyl, propyl, butyl or tert-butyl. The substituent $R_4$ has the same meaning as $R_1$, $R_2$ or $R_3$, but may additionally be hydrogen.

The base may in principle be any compound whose basicity is higher than that of the phenol. An alcoholate will normally be used, preferably an alkali metal alcoholate, especially one containing 1 to 4 carbon atoms, such as sodium or potassium methanolate or sodium or potassium tert-butylate. An alkali metal hydroxide, such as sodium or potassium hydroxide, or the phenolate formed therewith from the phenol of formula (2), can also act as a catalyst.

Up to the step of the neutralisation of the base, the process of this invention can be carried out in known manner, for example as described in the cited literature. It can be advantageous to add water to the reaction mixture after the addition of the compound of formula (3) and before the neutralisation, especially if compounds of formula (2) are to be reacted in which one of the substituents $R_1$ and $R_2$ is, for example, methyl. In this case, 0.1 to 1% of water (based on the weight of added compound of formula (3)) will preferably be added.

In the process of the invention, the base is neutralised with a carboxylic acid, preferably formic acid or acetic acid. The reaction mixture is filtered in the normal manner to remove the formate or acetate, as it has been found that these salts interfere with the subsequent rectification and can promote the elimination of the substituents $R_1$ and $R_2$. Neutralisation and filtration are preferably carried out in the temperature range from 50° to 130° C., preferably from 70° to 110° C.

The amount of carboxylic acid added conveniently corresponds to at least the equivalent amount of base present in the reaction mixture. It is preferred to use an excess of acid, for example of up to 50%.

To isolate the compounds of formula (1) it is preferred to use two continuously operating rectifying columns which are operated under reduced pressure. The more volatile by-products are separated as head product in the first column, while the less volatile by-products are separated as bottom product in the second column. The purified compound of formula (1) forms the distillate in the second column.

It is also possible to separate the less volatile by-products in the first column. The more volatile by-products are then removed in the second column, and the purified compound of formula (1) is subsequently obtained as bottom product.

As an alternative to using two continuously operating rectifying columns it is also possible to use a single continuously operating rectifying column which has a side outlet. In this case, the rectification is carried out such that more volatile by-products are obtained as head product and the less volatile products as bottom product. The purified compound of formula (1) is drawn off through a side outlet. If the side outlet is positioned between the feed and the bottom, then the compound of formula (1) is collected from the gas phase. It is collected from the liquid phase if the side outlet is positioned between the head and the feed.

The first of the two continuously operating rectifying columns is preferably a vacuum column which has a stripping section as well as a rectifying section. Excess phenol and the corresponding quinone (usually a coloured component) are separated in this column as head product. It is expedient to choose a very low head pressure (for example 3 mbar) and also to keep the pressure drop over the packing small in order to minimise thermal damage. The required reflux ratio depends substantially on the nature and amount of the phenol to be separated.

The less volatile impurities are separated from the product in the second rectifying column which, for the same reasons, is expediently operated at the same low pressures as the first column. The purified product is obtained as distillate. The required reflux ratio is normally not great (for example 1:1) and it is often possible to dispense with a stripping column without appreciable amounts of product passing into the bottom product.

Prior to rectification, the reaction mixture expediently passes an evaporator which operates at higher pressure than the rectifying columns. Conventional evaporators such as falling film evaporators and thin-film evaporators may be used. It is also possible to connect two such evaporators in series. The purpose of these evaporators is to vaporise (degas) very low boiling components such as water, carboxylic acid and acrylates, to a minimum tolerable residual concentration before rectification.

The evaporators will preferably operate at a pressure of 20 to 200 mbar, whereas the head pressure in the rectifying columns will preferably be in the range from 1 to 30 mbar.

The crude mixture issuing from the degassing can, at the pressure prevailing at the feed inlet of the column, be superheated, so that a flash evaporation takes place here. This factor must be taken into account when designing the column.

In the process of this invention, the neutralised and filtered reaction mixture can also be rectified batchwise. Required for this purpose are a still, with or without stirrer, a column with an efficient vacuum packing, condenser, reflux divider and a number of containers for the different fractions. A column efficiency of ten theoretical steps is normally sufficient, but is not absolutely necessary. By way of exemplification, individual fractions are listed below with the relevant data pertaining to reflux ratio and head pressure:

|  | Reflux ratio | Head pressure (mbar) |
| --- | --- | --- |
| 1st fraction (very low boiling components): | 0 | 20–200 |
| 2nd fraction (incl. phenols): | ≧2:1 | 1–30 |
| 3rd fraction (phenols and compounds of formula (1)) | ≧2:1 | 1–30 |
| 4th fraction (purified compounds of formula (1)) | ≦1:1 | 1–30 |
| 5th fraction (product and less volatile components): | ≦1:1 | 1–30 |

The first fraction corresponds to the degassing in continuous rectification. When the amount is very small, it does not pass into the condenser at all but is retained by the column packing. It then escapes into the vacuum pump when the pressure is lowered for the second fraction. The second fraction contains the phenols and is regarded as waste product. The reflux ratio depends substantially on how much product will be tolerated in this fraction. The third and fifth fractions are intermediate fractions which are conveniently mixed with the next batch. If in time an accumulation of unwanted by-products in these fractions occurs, then they must be partially or wholly discarded from time to time.

In the process of this invention it is preferred to prepare those compounds of formula (1), wherein $R_1$ is tert-butyl, $R_2$ is methyl or tert-butyl, $R_4$ is hydrogen and $R_3$ is methyl. The base is neutralised after the Michael addition with formic or acetic acid. The reaction mass is then filtered and, to isolate the compound of formula (1), fractionated in a continuously operated rectification apparatus comprising an evaporator and two continuously operating rectifying columns, the first of which has a stripping section as well as a rectifying section and the second a rectifying section only.

Figure 2:
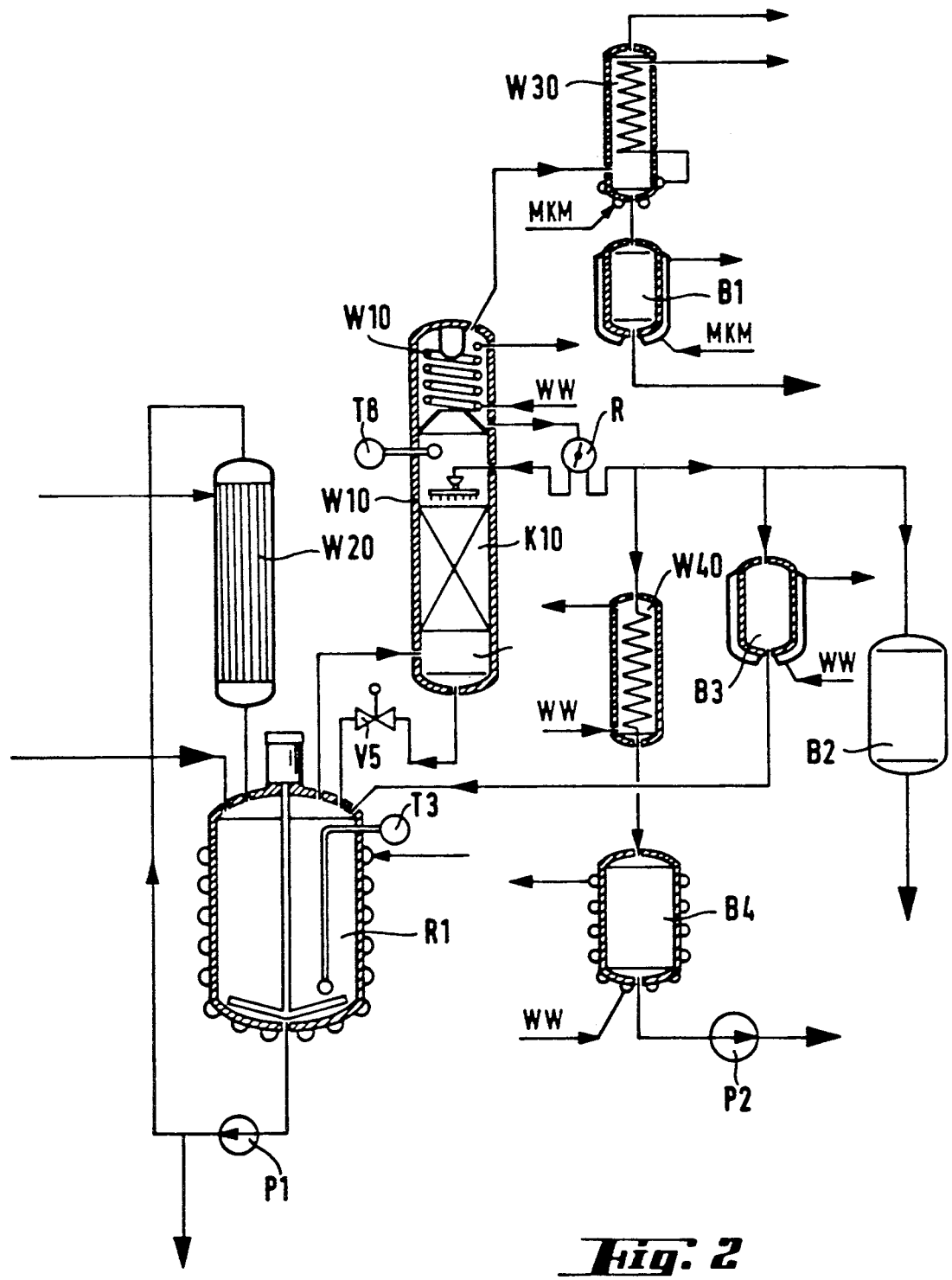

FIGS. 1 and 2 illustrate apparatus for the continuous and batchwise operation of the rectification.

In FIG. 1, the lines numbered 1 to 7 are mass flows, 1 being the mass flow of the crude product and 7 the mass flow of the pure product. The mass flows 2, 4 and 6 illustrate the separation of by-products. The mass flows 3 and 5 show the stepwise purification of the crude product. K1 and K2 are rectifying columns, K1 having a rectifying section and a stripping section and K2 having a rectifying section only. W1, W3 and W3 are evaporators, whereas W2, W4 and W6 are condensers. A more detailed description of this continuous apparatus will be found in Example 1.

The batchwise rectification of the crude product is illustrated in FIG. 2. The stirred vessel K1 is connected to the rectifying column K10 on which the condenser W10 is mounted. W30 and W40 are coolers, and W20 acts as evaporator. The containers B1 to B4 are for collecting the different fractions. R is a reflux divider, and P1 and P2 are pumps. An exact description of the mode of operation is provided in Example 2.

The invention is illustrated by the following non-limitative Examples in which, as well as in the claims and the remainder of the specification, percentages are by weight, unless otherwise stated.

EXAMPLE 1

Methyl 3,5-di-tert-butyl-4-hydroxyphenyl-1-propionate is prepared by addition of methyl acrylate to 2,6-di-tert-butylphenol. This is done by adding 6.5 g of aqueous 50% potassium hydroxide to a melt of 600 g of 2,6-di-tert-butylphenol, under nitrogen, to form potassium phenolate. Water is thereafter removed by distillation at a temperature of 100° C. and under a pressure of 20 mbar, and the reaction is carried out with 325 g of methyl acrylate at ca. 110° C. under normal pressure. Excess methyl acrylate is removed by vacuum distillation (10 mbar) at 115° C., and then reaction mixture is coold to 90° C. and neutralised with 2.8 g of formic acid (100%). The precipitated potassium formate is then removed by filtration at 90° C., giving a crude mixture of methyl 3,5-di-tert-butyl-4-hydroxyphenyl-1-propionate.

The crude mixture of methyl 3,5-di-tert-butyl-4-hydroxyphenyl-1-propionate so obtained (filtrate) is purified in a continuously operating laboratory rectifying apparatus which is illustrated in FIG. 1. The crude mixture is fed at a mass flow of 1212 g/h into the falling-film evaporator W1 (flow 1), where it is heated to 185° C./103 torr and in the process degassed. The escaping vapours are condensed in the condenser W2 (flow 2). The degassed crude mixture is fed into the column K1 (flow 3) and meanwhile cooled in the line to ca. 115° C., thereby avoiding a flash evaporation on entering the column K1. The head pressure of this column is 2.6 torr and the pressure in the bottom is ca. 7.2 torr. The vapours are condensed in the condenser W4 and some are removed and some are returned to the column. A temperature measured approximately in the middle of the rectifying section is controlled by means of the reflux ratio. The reflux ratio is thus subject to certain fluctuations, but is always greater than 10:1. In K1 the more volatile by-products are separated as head product (flow 4). A thin-film evaporator (W3) is used as reboiler. The temperature in the head is ca. 96° C. and in the bottom ca. 181° C. The mixture passes from the bottom of the column K1 into the reboiler W5 of the column K2 (flow 5). This reboiler is also a thin-film evaporator. The vapours of the column are condensed in the condenser W6, and are partly removed as purified product (flow 7) and partly returned to the column. The reflux ratio in the column K2 is 1:1. The less volatile by-products leave the column as bottom product (flow 6). The head pressure of the column K2 is 2.6 torr and the bottom pressure is ca. 6.2 torr. The temperature in the head is ca. 163° C. and, below the column packing, is ca. 186° C.

The crude mixture (flow 1) contains 94.3% of methyl 3,5-di-tert-butyl-4-hydroxyphenyl-1-propionate, 0.9% of 2,6-di-tert-butylphenol, 0.8% of 2,4-di-tert-butylphenol, traces of methyl acrylate and water, as well as largely unknown by-products, some of which are coloured. The purified product (flow 7) contains 99.5% of methyl 3,5-di-tert-butyl-4-hydroxyphenyl-1-propionate, no phenols and no coloured by-products. The phenols remain in flow 4, and some of the coloured by-products remain in flow 4 and some in flow 6. More than 99% of the methyl 3,5-di-tert-butyl-4-hydroxyphenyl-1-propionate present in flow 1 are found again in flow 7.

All apparatus parts are of glass and only certain parts are of stainless steel (e.g. rotor shafts of the thin-film evaporators W3 and W5). The columns K1 and K2 have an internal diameter of 50 mm and are vacuum insulated. The packing consists of 8×8 mm wire mesh rings with flange (material: stainless steel). The packing height in K1 in the rectifying section is 32 cm and in the stripping section 32 cm, and in K2 in the rectifying section 45 cm.

The thin-film evaporators W3 and W5 have a heating surface of 0.06 m², and the falling-film evaporator W1 has a heating surface of similar size.

EXAMPLE 2

In accordance with the procedure described in Example 1, methyl 3-methyl-5-tert-butyl-4-hydroxyphenyl-1-propionate is prepared by addition of methyl acrylate to 2-methyl-6-tert-butylphenol, 0.4% of water (based on methyl acrylate) being added 3 hours after the addition of methyl acrylate.

After the reaction, excess methyl acrylate is removed by vacuum distillation, while ensuring that the wall temperature of the reactor does not exceed 115° C., and the reaction mixture is neutralised with formic acid. The precipitated potassium formate is removed at 90° C. by filtration. Purification of the crude product is subsequently effected by rectification.

The synthesis is carried out batchwise in a production plant in a 6.3 m³ reactor. A helical filter (filter area: 12.6 m²), in which the filtration of a batch is carried out in not more than 1 hour, is used for filtration. The filtered crude mixture is rectified batchwise. The rectifying apparatus is illustrated in FIG. 2. It consists of a stirred vessel R1, a rectifying column K10 on which a coil condenser W10 is mounted, and an external reflux divider R, a condenser W30 used as cooling trap, a coiled spray cooler W40 used as distillate cooler, and falling-film evaporator W20 over which the contents of the stirred vessel are circulated by means of the pump P1. W20 is used for increasing the rate of evaporation. The different fractions are collected in the containers B1 to B4. All apparatus is of stainless steel. The characteristic dimensions are: (F=heat exchange area, V=nominal volume):

| | |
|---|---|
| R1: | V = 6.3 m³ |
| W10: | F = 16. m² |
| W20: | F = 32 m² |
| W30: | F = 2.5 m² |
| B1: | V = 0.1 m³ |
| B2: | V = 0.63 m³ |
| B3: | V = 0.25 m³ |
| B4: | V = 0.63 m³ |
| K10: | diameter: 1.2 m |
| | packing height: 2.73 m |
| | packing: Mellapak 350 Y (Sulzer) |

In apparatus W10, W40, B3 and B4 warm water (WW) is used as cooling and heating medium. It must have a temperature of ca. 50° C., as the methyl 3-methyl-5-tert-butyl-4-hydroxyphenyl-1-propionate has a melting point of 44.5° C. W30 and B1 are cooled with methanol (MKM), which has a temperature of ca. −35° C.

A filtered batch contains ca. 84.3% of methyl 3-methyl-5-tert-butyl-4-hydroxyphenyl-1-propionate, 4.1% of 3-methyl-5-tert-butylphenol, 0.1 to 0.2% of formic acid, and traces of methyl acrylate and possible traces of water. The remainder consists principally of less volatile by-products. Before the start of the rectification, the intermediate fraction and the final fraction of the preceding batch are mixed (fractions 3 and 5). First the reactor contents are heated to 155° C. at total reflux, and the apparatus is simultaneously evacuated to 20 mbar, whereupon the very volatile components, such as methyl acrylate, formic acid and water, escape into the cooling trap W3 and are collected as condensate in the container B1. After waiting for ca. 15 minutes, the condensate is removed from B1 (fraction 1). The head pressure is then lowered to 4 mbar and the reactor contents are successively heated until the onset of total reflux. Then fraction 2 is obtained at a reflux ratio of 1:1 and collected in B2 (phenol fraction). It is complete when the head temperature has reached a value T8≈110° C. Fraction 3 is obtained at a reflux ratio of 3:1 and collected in B3. It is complete when the head temperature has reached a value T8≈160° C. (intermediate fraction). These limiting temperatures are only standard values which must be optimised when starting up. Fraction 4 (purified product) is removed without reflux and collected in the container B4, which is emptied from time to time by means of the pump P2. This fraction is complete when the internal temperature has reached the value T3≈192° C. The column is then set to total reflux, the discharge valve V5 is closed, and fraction 5 is collected in the bottom part of the column (final fraction). It is complete when the internal temperature has reached the value T3≈196° C. These limiting temperatures too are only standard values which must be optimised when starting up.

The following amounts of the individual fractions are to be expected for a batch (filtered crude mixture) of 6342 g when, at the start, fractions 3 and 5 of the previous batch are also added:

| 1. fraction | 38 kg |
| --- | --- |
| 2. fraction (phenol frac.) | 342 kg |
| 3. fraction (intermed. frac.) | 58 kg |
| 4. fraction (product) | 5371 kg |
| 5. fraction (final frac.) | 101 kg |
| residue | 591 kg |

Fraction 4 contains ca. 97.6% of methyl 3-methyl-5-tert-butyl-4-hydroxyphenyl-1-propionate, and the losses of methyl 3-methyl-5-tert-butyl-4-hydroxyphenyl-1-propionate during the rectification are ca. 2%. Given the above amounts, vapours which escape into the vacuum pump are included in fraction 1. The rectification of a batch of the above size, including filtration, takes at most 12 hours.

What is claimed is:

1. An improved process for the preparation of a compound of formula

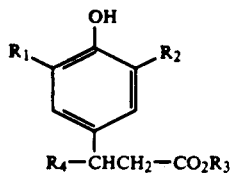
(1)

by reacting a compound of formula

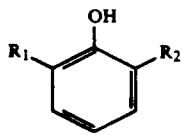
(2)

with a compound of formula

(3)

wherein the substituents $R_1$ to $R_3$ in formulae (1) to (3) are each independently of the other alkyl of 1 to 4 carbon atoms, and $R_4$ is hydrogen or alkyl of 1 to 4 carbon atoms, in the presence of a base, and isolating the compound of formula (1), wherein the improvement comprises adding a carboxylic acid to the reaction mixture to neutralize the base after the reaction of a compound of formula (2) with a compound of formula (3) and before the isolation of a compound of formula (1), filtering the reaction mixture, and rectifying the filtrate to isolate the compound of formula (1).

2. A process according to claim 1, wherein formic acid or acetic acid is used for neutralizing the base.

3. A process according to claim 1, wherein neutralization and filtration are carried out in the temperature range from 50° to 130° C.

4. A process according to claim 1, wherein the compound of formula (1) is isolated by using two continuously operating rectifying columns, under reduced pressure, to separate less volatile and more volatile by-products from said compound.

5. A process according to claim 1, wherein the compound of formula (1) is isolated by using a continuously operating rectifying column with a side outlet to draw off said compound from said side outlet.

6. A process according to claim 4, wherein an evaporator is upstream of the continuously operating rectifying columns or the continuously operating rectifying column with side outlet, which evaporator is operated at a pressure higher than that in the columns or column with side outlet.

7. A process according to claim 4, wherein the head pressure of the rectifying columns or column with side outlet is 1 to 30 mbar.

8. A process according to claim 6, wherein the pressure in the evaporator is 20 to 200 mbar.

9. A process according to claim 1, wherein the compound of formula (1) is isolated by using a batchwise operating rectifying column, under reduced pressure, to separate less volatile and more volatile by-products therefrom.

10. A process according to claim 1 for the preparation of compounds of formula (1), wherein $R_1$ is tert-butyl, $R_2$ is methyl or tert-butyl, $R_4$ is hydrogen and $R_3$ is methyl, by reacting a compound of formula (2), wherein $R_1$ and $R_2$ have the given meanings, with a compound of formula (3), wherein $R_3$ and $R_4$ have the given meanings, in the presence of a base, which process comprises neutralizing the base by adding formic or acetic acid to the reaction mass after the reaction of a compound of formula (2) with a compound of formula (3) and before the isolation of the compound of formula (1), then filtering the reaction mass and, to isolate the compound of formula (1) from said reaction mass, using a rectification apparatus comprising an evaporator and two continuously operating rectifying columns connected in series, the first of which two columns has a stripping section as well as a rectifying section and the second a rectifying section only.

11. A process according to claim 10 for the preparation of a compound of formula (1), wherein $R_1$ is tert-butyl, $R_2$ is methyl, $R_4$ is hydrogen and $R_3$ is methyl, by reacting a compound of formula (2), wherein $R_1$ and $R_2$ have the given meanings, with a compound of formula (3), wherein $R_3$ and $R_4$ have the given meanings, in the presence of a base, which process comprises adding water to the reaction mass after the reaction of a compound of formula (2) with a compound of formula (3) and before neutralization.

* * * * *